United States Patent
Radbruch et al.

(10) Patent No.: US 9,862,772 B2
(45) Date of Patent: Jan. 9, 2018

(54) COMPOSITIONS AND METHODS (71) Applicant: Deutsches Rheuma-Forschungszentrum Berlin (DRFZ), Berlin (DE)

(72) Inventors: Andreas Radbruch, Berlin (DE); Falk Hiepe, Berlin (DE); Adriano Taddeo, Berlin (DE); Velia Gerl, Berlin (DE); Bimba F. Hoyer, Berlin (DE); Hyun-Dong Chang, Berlin (DE); Andreas Theiel, Berlin (DE)

(73) Assignee: BEUTSCHES RHEUMA-FORSCHUNGSZENTRUM BERLIN (DRFZ), Berlin (DE)

( * ) Notice: Subject to any disclaimer, the term of this patent is extended or adjusted under 35 U.S.C. 154(b) by 34 days.

(21) Appl. No.: 14/426,650

(22) PCT Filed: Sep. 6, 2013

(86) PCT No.: PCT/EP2013/068503
§ 371 (c)(1),
(2) Date: Mar. 6, 2015

(87) PCT Pub. No.: WO2014/037519
PCT Pub. Date: Mar. 13, 2014

(65) Prior Publication Data
US 2015/0239979 A1 Aug. 27, 2015

(30) Foreign Application Priority Data
Sep. 7, 2012 (GB) .................................. 1216002.4

(51) Int. Cl.
*A61K 39/395* (2006.01)
*C07K 16/28* (2006.01)
*C07K 14/77* (2006.01)
*C07K 14/47* (2006.01)
*A61K 39/00* (2006.01)
*G01N 33/569* (2006.01)

(52) U.S. Cl.
CPC ...... *C07K 16/2896* (2013.01); *A61K 39/0008* (2013.01); *A61K 39/3955* (2013.01); *C07K 14/4713* (2013.01); *C07K 14/77* (2013.01); *C07K 16/2884* (2013.01); *G01N 33/56972* (2013.01); *A61K 2039/505* (2013.01); *A61K 2039/507* (2013.01); *C07K 2317/732* (2013.01); *C07K 2317/734* (2013.01); *C07K 2319/00* (2013.01); *C07K 2319/33* (2013.01); *C07K 2319/70* (2013.01); *C07K 2319/74* (2013.01); *G01N 2800/24* (2013.01)

(58) Field of Classification Search
None
See application file for complete search history.

(56) References Cited

U.S. PATENT DOCUMENTS

2009/0202487 A1 8/2009 Chang
2010/0291105 A1 11/2010 Von Strandmann

FOREIGN PATENT DOCUMENTS

| EP | 1388544 | 2/2004 |
|---|---|---|
| WO | WO 96/16990 | 6/1996 |
| WO | WO 99/62526 | 12/1999 |
| WO | WO 2007/035857 | 3/2007 |
| WO | WO 2008/097439 | 8/2008 |
| WO | WO 2010/022225 | 2/2010 |
| WO | WO 2012/030982 | 8/2012 |
| WO | WO 2014/037519 | 3/2014 |

OTHER PUBLICATIONS

Burton, et al., "CD74 is expressed by multiple myeloma and is a promising target for therapy," Clinical Cancer Research, 10(19):6606-6611, 2004.
Hiepe, et al., "Long-lived autoreactive plasma cells drive persistent autoimmune inflammation," Nature Reviews Rheumatology, 7(3):170-178, 2011.
International Search Report for PCT/EP2013/068503, dated Apr. 15, 2014, 8 pages.
Meager, et al., "Anti-cytokine autoantibodies in autoimmunity: preponderance of neutralizing autoantibodies against interferon-alpha, interferon-omega and interleukin-12 in patients with thymoma and/or myasthenia gravis," Clinical Experimental Immunology, 132(1):128-136, 2003.
Pinto, et al., "A functional BCR in human IgA and IgM plasma cells," Blood, 121(20):4110-4114, 2013.
Song, et al., "Autoantibodies in rheumatoid arthritis: rheumatoid factors and anticitrullinated protein antibodies," QJ Med, 103(3):139-146, 2010.
Xiang, et al., "FcgammaRIIb controls bone marrow plasma cell persistence and apoptosis," Nature Immunology, 8(4):419-429, 2007.
Taddeo, A., et al., "Selection and Depletion of Plasma Cells Based on the Specificity of the Secreted Antibody," Eur. J. Immunol. 2015, vol. 45, pp. 317-319.

*Primary Examiner* — Sheela J. Huff
(74) *Attorney, Agent, or Firm* — Cooley LLP (57) ABSTRACT

The invention relates to a composition comprising an anchor region capable of binding to a plasma cell; and a binding region associated with the anchor region, wherein the binding region binds a specific plasma cell antibody.

19 Claims, 3 Drawing Sheets

Figure 1a

4C9 anti-ova secreting cells

COMPOSITIONS AND METHODS

This application is a National Stage filing of PCT Application No. PCT/EP2013/068503 filed Sep. 6, 2013 which claims priority to GB Application No. 1216002.4, filed Sep. 7, 2012, the contents of each of which are incorporated by reference herein in their entirety.

The present invention relates to compositions and methods suitable for the elimination and the selection of antibody secreting cells, and in vivo, for example in the treatment of diseases associated with the production of antibodies by plasma cells.

BACKGROUND OF THE INVENTION

Plasma cells (PC) are antibody secreting cells (ASC) that play a central role in humoral immunity by producing protective antibodies. However, in many autoimmune diseases and in allergy long-lived PC secreting autoantibodies contribute to immunopathology (1). Long-lived PC reside in specialized survival niches and do not proliferate. They are refractory to therapies that target the activation and/or proliferation of lymphocytes (e.g. cyclophosphamide, immunosupressants, and glucocorticoids) (2). They are also not affected by the depletion of their precursors, the B-lymphocytes, with the monoclonal anti-CD20 antibody as PC do not express CD20 (1). Thus, current therapies do not affect autoantibody production and do not have curative potential. Deletion of autoantibody-secreting PC poses a major challenge and seems to be critical to reach long-term, therapy-free remission. Current strategies to deplete PC, such as anti-thymocyte globulin (ATG) (3), proteasome blockade by bortezomib (4), anti-VLA4/anti-LFA1 antibodies (5), or TACI-Ig, are more or less effective, lack selectivity, and often have unwanted side-effects. A selective depletion of antigen-specific PC would limit side-effects and preserve protective antibody titres.

The present invention addresses the issue of elimination of plasma cells secreting specific antibodies

STATEMENT OF INVENTION

The present invention relates to

A composition comprising:
an anchor region capable of binding to a plasma cell; and
a binding region associated with the anchor region, wherein the binding region is capable of binding a specific plasma cell antibody.

A nucleic acid encoding a composition of the invention.

A method for prevention or treatment of disease, the method comprising delivery to an individual a composition comprising:
an anchor region capable of specific binding to a plasma cell; and
a binding region associated with the anchor region, wherein the binding region is capable of binding a specific plasma cell antibody A method for the in vitro-elimination of antigen-specific antibody secreting cell, the method comprising contacting a sample comprising an antibody secreting cell with a composition comprising: an anchor region capable of binding to a plasma cell; and
a binding region associated with the anchor region, wherein the binding region is capable of binding a specific plasma cell antibody Use of a composition comprising:
an anchor region capable of binding to a plasma cell; and
a binding region associated with the anchor region, wherein the binding region is capable of binding a specific plasma cell antibody
in the preparation of a medicament for prevention or treatment of disease in an individual caused or exacerbated by an antibody released by the plasma cell, A composition comprising:
an anchor region capable of binding to a plasma cell; and
a binding region associated with the anchor region, wherein the binding region is capable of binding a specific plasma cell antibody;
for use in prevention or treatment of disease caused or exacerbated by an antibody released by the plasma cell, wherein the composition is delivered to an individual.

A composition comprising:
an anchor region capable of binding to a plasma cell; and
a binding region associated with the anchor region, wherein the binding region is capable of binding a specific plasma cell antibody,
the composition for use in elimination of an antibody released by the plasma cell, wherein the composition is delivered to an individual, such as a human or non-human animal.

A method for elimination of an antibody released by a plasma cell, the method comprising delivering to an individual, such as a human or non-human animal, a composition comprising:
an anchor region capable of binding to a plasma cell; and
a binding region associated with the anchor region, wherein the binding region binds a specific plasma antibody.

DETAILED DESCRIPTION OF THE INVENTION

In one aspect the invention provides a method for antigen specific-elimination of ASC (e.g. plasma cells) based on the specificity of the antibodies secreted by the cells. The invention is therefore able to cause the self-elimination of antigen-specific ASC. This is achieved by labelling ASC with a composition comprising:
an anchor region capable of binding to a plasma cell; and
a binding region associated with the anchor region, wherein the binding region is capable of binding a specific plasma cell antibody.

That composition may comprise, for example, an antibody binding specifically to ASC (the anchor region) associated with an autoantigen specific to the antibodies secreted by the (to be eliminated) ASC, where the autoantigen is or forms a part of the binding region. The specific antibodies secreted by the ASC will bind to the antigen brought to the surface of the ASC. The ASC can then be killed by complement lysis and/or antibody-dependent cellular cytotoxicity (ADCC). The "suicide" of the ASC is specific for the cells that secrete the specific antibodies directed towards the antigen of interest and does not affect ASC of other specificities or other cells types (e.g. B and T cells, stem cells, etc.).

In one aspect an anchor region is capable of binding to an antigen on the surface of a plasma cell. In one aspect the affinity constants for the interaction of the anchor region or composition comprising the anchor region with a cell surface antigen, may be in the range of $10^6$ to $10^9$ $M^{-1}$, or may be greater than $10^6$, greater than $10^7$, greater than $10^8$ or greater than $10^9$ $M^{-1}$.

In one aspect an anchor region capable of binding to a plasma cell means that the anchor region will preferentially bind to plasma cells with reduced or no or minimal binding in comparison to another cell type e.g. B and T lymphocytes. Minimal binding might be less than 50%, eg less than 40%, less than 30%, less than 20% or less than 10% of the binding to other cell types, eg B cells or T cells, as assessed by eg association or dissociation constants. Suitably specific binding can be achieved by binding to molecules that are mainly or uniquely found on the surface of the plasma cell, or are found at a higher number on plasma cells than on other cell types, eg than B cell or T cells.

In one aspect the anchor region binds to a plasma cell with at least 2 fold greater affinity, such as at least 5 fold greater, 10 fold greater, 50 fold greater, 100 fold greater, or more affinity, with respect to a non plasma cell, such as a B or T cell.

In one aspect the anchor region binds to a plasma cell in at least a 2 fold greater number, such as at least 5 fold greater, 10 fold greater, 50 fold greater, 100 fold greater number, or more, than it binds to a non plasma cell, such as a B or T cell.

In one aspect the binding of the anchor region to a plasma cell can be distinguished from binding of the same anchor region to another (non plasma cell), by analysis of cell killing as described in assays herein, wherein suitably specific binding of the anchor region gives an increase in cell killing of plasma cells vs non plasma cells, such as B or T cells, generally in the order of 2 fold, 3 fold, 4 fold, 5 fold, 10 fold, 50 fold, 100 fold or even more. In this way the cell killing as described in the invention is preferential for plasma cells.

In one aspect the anchor region, which may be an antibody or part thereof, specifically binds one or more of CD138, CD38 or BCMA.

In one aspect the anchor region is a polypeptide which consists of, or comprises, an antibody or antigen binding fragment thereof. In one aspect the antibody or binding fragment thereof is capable of binding to an antigen located on the surface of a plasma cell.

The anchor region of the composition of the invention may comprise an antibody or an antigen binding fragment thereof, for example may comprise a bivalent fragment such as (Fab')2, monovalent fragments such as Fab, single chain antibodies, Fv fragments including single chain Fv (scFv), single domain antibodies, multivalent single chain antibodies, diabodies, triabodies, and the like that bind specifically with an antigen. Antibody binding fragments can include polyclonal and monoclonal antibodies or antigen binding fragments thereof. Antibodies or fragments may be of any class such as IgG, IgM, IgA, IgE or IgD. The antibody or fragment thereof may be a bispecific antibody with specificity for two different plasma cell antigens, such as CD138 and CD38, for example.

Antibodies or antigen binding fragments may be humanised in whole or in part.

Suitably the composition of the invention is not immunogenic in humans.

The person skilled in the art is familiar with methods for generation of antibodies and fragments thereof which are specific for a given target. Antibodies are readily raised in animals such as rabbits or mice by immunization with the gene product, or a fragment thereof. Immunized mice can provide sources of B cells for the manufacture of hybridomas, which in turn are cultured to produce large quantities of monoclonal antibodies. These antibodies, and the nucleic acids encoding them, can be used to generate the composition of the present invention. For example, if necessary, nucleic acid encoding an antibody or part thereof which forms the anchor region can be cloned and then ligated to a nucleic acid encoding a binding region, followed by expression in an appropriate expression system to generate the composition of the invention.

For preparation of monoclonal or polyclonal antibodies, any technique known in the art can be used (see, e.g., Kohler & Milstein, Nature 256:495-497 (1975); Kozbor et al., Immunology Today 4: 72 (1983); Cole et al., pp. 77-96 in Monoclonal Antibodies and Cancer Therapy (1985)). Techniques for the production of single chain antibodies (U.S. Pat. No. 4,946,778) can be adapted to produce antibodies to polypeptides of this invention. Also, transgenic mice, or other organisms such as other mammals, may be used to express humanised antibodies. Alternatively, phage display technology can be used to identify antibodies and heteromeric Fab fragments that specifically bind to selected antigens (see, e.g., McCafferty et al., Nature 348:552-554 (1990); Marks et al., Biotechnology 10:77 O-7 '83 (1992)).

Likewise, techniques for humanising antibodies are also well known in the art, as are techniques for the production of fully humanised antibodies in mice.

In one aspect the anchor region comprises a variable lymphocyte receptor (VLR) or antigen binding part thereof, for example a VLR specific for a plasma cell antigen, (see Annu Rev Immunol. 2012; 30:203-20. Epub 2012 Jan. 3. VLR-based adaptive immunity. Boehm T, McCurley N, Sutoh Y, Schorpp M, Kasahara M, Cooper M D.)

In one aspect the features disclosed herein in respect of the anchor region apply equally to the composition comprising the anchor region in association with a binding region.

The binding region is capable of binding to a specific plasma cell antibody, suitably an antibody released by the cell to which the anchor region is capable of binding. In one aspect the binding region will not interact with all antibodies in the body. In one aspect the binding region is not an antibody or part thereof directed to the constant region or other shared regions of another antibody or part thereof. In one aspect the binding region interacts with the antibody product of one plasma cell or cell line preferentially to the interaction with antibodies of other plasma cells.

In one aspect the binding region displays preferential binding to an antibody which is an antibody against an autoantigen, an antigen related to therapy resistance, or an allergen.

In a similar way to the interaction between anchor and plasma cell, the interaction between the binding region and plasma cell antibody may have an affinity constant in the range of $10^6$ to $109^{M-}$, or may be greater than $10^6$, greater than $10^7$, greater than $10^8$ or greater than $10^{9\ M-1}$.

In one aspect reference to the 'binding region mediating specific binding to a plasma antibody' herein can mean that the binding region can serve, for example, as a ligand (which may also be referred as a target) for a plasma cell antibody released from a plasma cell. Thus in one preferred aspect the binding region is a target for a plasma antibody. In one aspect the binding region may be bound by the variable region of a secreted antibody, such as the CDRs of the antibody released by the plasma cell.

In another aspect the binding region can bind to a specific plasma cell antibody ligand. In one aspect the binding region may comprise an antibody, or antigen binding fragment thereof, which is capable of binding to a specific antibody released by a plasma cell, in one aspect being specific for the variable portion, or part thereof, of that plasma antibody.

In one aspect the binding region comprises an antigen associated with disease.

Diseases that may be addressed by the present invention include those associated with host antibody production and include, for example autoimmune disease and allergy.

An autoimmune disease herein is a disease arising from and directed against an individual's own tissues or a co-segregate or manifestation thereof or resulting condition therefrom. Examples of autoimmune diseases or disorders include, but are not limited to arthritis (rheumatoid arthritis, juvenile-onset rheumatoid arthritis, osteoarthritis, psoriatic arthritis, and ankylosing spondylitis), psoriasis, vitiligo, dermatitis including atopic dermatitis, chronic idiopathic urticaria, including chronic autoimmune urticaria, polymyositis/dermatomyositis, toxic epidermal necrolysis, scleroderma (including systemic scleroderma), sclerosis such as progressive systemic sclerosis, inflammatory bowel disease (IBD) (for example, Crohn's disease, ulcerative colitis, autoimmune inflammatory bowel disease), pyoderma gangrenosum, erythema nodosum, primary sclerosing cholangitis, episcleritis), respiratory distress syndrome, including adult respiratory distress syndrome (ARDS), meningitis, IgE-mediated diseases such as anaphylaxis and allergic and atopic rhinitis, encephalitis such as Rasmussen's encephalitis, uveitis or autoimmune uveitis, colitis such as microscopic colitis and collagenous colitis, glomerulonephritis (GN) such as membranous GN (membranous nephropathy), idiopathic membranous GN, membranous proliferative GN (MPGN), including Type I and Type II, and rapidly progressive GN, allergic conditions, allergic reaction, eczema, asthma, conditions involving infiltration of T cells and chronic inflammatory responses, atherosclerosis, autoimmune myocarditis, leukocyte adhesion deficiency, systemic lupus erythematosus (SLE) such as cutaneous SLE, subacute cutaneous lupus erythematosus, lupus (including nephritis, cerebritis, pediatric, non-renal, discoid, alopecia), juvenile onset (Type I) diabetes mellitus, including pediatric insulin-dependent diabetes mellitus (IDDM), adult onset diabetes mellitus (Type II diabetes), multiple sclerosis (MS) such as spino-optical MS, immune responses associated with acute and delayed hypersensitivity mediated by cytokines and T-lymphocytes, tuberculosis, sarcoidosis, granulomatosis including lymphomatoid granulomatosis, Wegener's granulomatosis, agranulocytosis, vasculitis (including large vessel vasculitis (including polymyalgia rheumatica and giant cell (Takayasu's) arteritis), medium vessel vasculitis (including Kawasaki's disease and polyarteritis nodosa), CNS vasculitis, systemic necrotizing vasculitis, and ANCA-associated vasculitis, such as Churg-Strauss vasculitis or syndrome (CSS)), temporal arteritis, aplastic anemia, Coombs positive anemia, Diamond Blackfan anemia, hemolytic anemia or immune hemolytic anemia including autoimmune hemolytic anemia (AIHA), pernicious anemia, pure red cell aplasia (PRCA), Factor VIII deficiency, hemophilia A, autoimmune neutropenia, pancytopenia, leukopenia, diseases involving leukocyte diapedesis, CNS inflammatory disorders, multiple organ injury syndrome, antigen-antibody complex mediated diseases, anti-glomerular basement membrane disease, antiphospholipid antibody syndrome, allergic neuritis, Bechet's or Behcet's disease, Castleman's syndrome, Goodpasture's syndrome, Reynaud's syndrome, Sjogren's syndrome, Stevens-Johnson syndrome, pemphigoid such as pemphigoid bullous, pemphigus (including vulgaris, foliaceus, and pemphigus mucus-membrane pemphigoid), autoimmune polyendocrinopathies, Reiter's disease, immune complex nephritis, chronic neuropathy such as IgM polyneuropathies or IgMmediated neuropathy, thrombocytopenia (as developed by myocardial infarction patients, for example), including thrombotic thrombocytopenic purpura (TTP) and autoimmune or immune-mediated thrombocytopenia such as idiopathic thrombocytopenic purpura (ITP) including chronic or acute ITP, autoimmune disease of the testis and ovary including autoimmune orchitis and oophoritis, primary hypothyroidism, hypoparathyroidism, autoimmune endocrine diseases including thyroiditis such as autoimmune thyroiditis, chronic thyroiditis (Hashimoto's thyroiditis), or subacute thyroiditis, autoimmune thyroid disease, idiopathic hypothyroidism, Addison's disease, Grave's disease, polyglandular syndromes such as autoimmune polyglandular syndromes (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis, myasthenia gravis, cerebellar degeneration, limbic and/or brainstem encephalitis, neuromyotonia, opsoclonus or opsoclonus myoclonus syndrome (OMS), Anti-myelin-associated glycoprotein (anti-MAG) neuropathy and sensory neuropathy, Sheehan's syndrome, autoimmune hepatitis, chronic hepatitis, lupoid hepatitis, chronic active hepatitis or autoimmune chronic active hepatitis, lymphoid interstitial pneumonitis, bronchiolitis obliterans (non-transplant) vs NSIP, GuillainBarre syndrome, Berger's disease (IgA nephropathy), primary biliary cirrhosis, celiac sprue (gluten enteropathy), refractory sprue, dermatitis herpetiformis, cryoglobulinemia, amyotrophic lateral sclerosis (ALS; Lou Gehrig's disease), coronary artery disease, autoimmune inner ear disease (AIED) or autoimmune hearing loss, opsoclonus myoclonus syndrome (OMS), polychondritis such as refractory polychondritis, pulmonary alveolar proteinosis, amyloidosis, giant cell hepatitis, scleritis, a non-cancerous lymphocytosis, a primary lymphocytosis, which includes monoclonal B cell lymphocytosis (e.g., benign monoclonal gammopathy and monoclonal gammopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal segmental glomerulosclerosis (FSGS), endocrine ophthalmopathy, uveoretinitis, autoimmune hepatological disorder, fibromyalgia, multiple endocrine failure, Schmidt's syndrome, adrenalitis, gastric atrophy, presenile dementia, demyelinating diseases, Dressler's syndrome, alopecia areata, CREST syndrome (calcinosis, Raynaud's phenomenon, esophageal dysmotility, sclerodactyly, and telangiectasia), male and female autoimmune infertility, ankylosing spondolytis, mixed connective tissue disease, Chagas' disease, rheumatic fever, recurrent abortion, farmer's lung, erythema multiforme, post-cardiotomy syndrome, Cushing's syndrome, bird-fancier's lung, Alport's syndrome, alveolitis such as allergic alveolitis and fibrosing alveolitis, interstitial lung disease, transfusion reaction, leprosy, malaria, leishmaniasis, kypanosomiasis, schistosomiasis, ascariasis, aspergillosis, Sampter's syndrome, Caplan's syndrome, dengue, endocarditis, endomyocardial fibrosis, endophthalmitis, erythema elevatum et diutinum, erythroblastosis fetalis, eosinophilic faciitis, Shulman's syndrome, Felty's syndrome, flariasis, cyclitis such as chronic cyclitis, heterochronic cyclitis, or Fuch's cyclitis, Henoch-Schonlein purpura, human immunodeficiency virus (HIV) infection, echovirus infection, cardiomyopathy, Alzheimer's disease, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes dorsalis, and giant cell polymyalgia.

As used herein, the term "allergy" or "allergies" refers to a disorder (or improper reaction) of the immune system. Allergic reactions occur to normally harmless environmental substances known as allergens; these reactions are acquired, predictable, and rapid. Strictly, allergy is one of four forms of hypersensitivity and is called type I (or immediate) hypersensitivity. It is characterized by excessive activation of certain white blood cells called mast cells and basophils by a type of antibody known as IgE, resulting in an extreme inflammatory response. Common allergic reactions include eczema, hives, hay fever, asthma, food allergies, and reactions to the venom of stinging insects such as wasps and bees. Mild allergies like hay fever are highly prevalent in the human population and cause symptoms such as allergic conjunctivitis, itchiness, and runny nose. Allergies can play a major role in conditions such as asthma. In some people, severe allergies to environmental or dietary allergens or to medication may result in life-threatening anaphylactic reactions and potentially death.

Autoimmune disease may be selected from systemic autoimmune diseases including SLE, Sjögren's syndrome, scleroderma, rheumatoid arthritis, and dermatomyositis or may be local syndromes which affect a specific organ or tissue. The latter may be selected from endocrinologic diseases such as: Diabetes mellitus type 1, Hashimoto's thyroiditis, Addison's disease; Gastrointestinal such as Coeliac disease, Crohn's Disease, Pernicious anaemia; Dermatologic diseases such as: Pemphigus vulgaris, Vitiligo; Haematologic diseases such as: Autoimmune haemolytic anaemia, Idiopathic thrombocytopenic purpura; Neurological diseases such as: Myasthenia gravis, Anti-myelin-associated glycoprotein (anti-MAG) neuropathy.

In one aspect the disease is one of: arthritis (rheumatoid arthritis, juvenile-onset rheumatoid arthritis, osteoarthritis, psoriatic arthritis, and ankylosing spondylitis), vitiligo, chronic autoimmune urticaria, inflammatory bowel disease (IBD) (for example, Crohn's disease, ulcerative colitis, autoimmune inflammatory bowel disease), IgE-mediated diseases such as anaphylaxis and allergic and atopic rhinitis, allergic conditions, allergic reaction, eczema, asthma, systemic lupus erythematosus (SLE) such as cutaneous SLE, subacute cutaneous lupus erythematosus, lupus (including nephritis, cerebritis, pediatric, non-renal, discoid, alopecia), juvenile onset (Type I) diabetes mellitus, including pediatric insulin-dependent diabetes mellitus (IDDM), adult onset diabetes mellitus (Type II diabetes), multiple sclerosis (MS) such as spino-optical MS, Factor VIII deficiency, hemophilia A, Sjogren's syndrome, thrombocytopenia (as developed by myocardial infarction patients, for example), including thrombotic thrombocytopenic purpura (TTP) and autoimmune or immune-mediated thrombocytopenia such as idiopathic thrombocytopenic purpura (ITP) including chronic or acute ITP, primary hypothyroidism, hypoparathyroidism, autoimmune endocrine diseases including thyroiditis such as autoimmune thyroiditis, chronic thyroiditis (Hashimoto's thyroiditis), or subacute thyroiditis, autoimmune thyroid disease, idiopathic hypothyroidism, Addison's disease, Grave's disease, Lambert-Eaton myasthenic, stiff-man or stiff-person syndrome, myasthenia gravis, Anti-myelin-associated glycoprotein (anti-MAG) neuropathy autoimmune hepatitis, GuillainBarre syndrome, celiac sprue (gluten enteropathy), allergy such as eczema, hives, hay fever, asthma, food allergies, and reactions to the venom of stinging insects such as wasps and bees, allergic conjunctivitis, itchiness, and runny nose.

In one aspect the antigen is a naturally occurring antigen found in a human or animal body.

In one aspect the antigen is not a part of an antibody naturally occurring in a human or animal body.

The disease may be an autoimmune disease. In one aspect the binding region comprises an autoantigen.

In one aspect the binding region comprises autoantigen associated with a disease selected from the diseases listed above, and for example may be from a systemic autoimmune disease or local syndrome, such as endocrinologic, gastrointestinal, dermatologic, hematologic or neurological diseases as discussed above.

In one aspect the autoantigen is, but not limited to, all or a part of: the nicotinic acetylcholine receptor, Muscarinic acetylcholine receptor M1, MuSK protein, myelina associated glycoprotein, 17 hydroxylase; 21 hydroxylase, cardiolipin, β2 glycoprotein I, phosphatidylserine, apoH, Annexin A5, Voltage-dependent calcium channel, Ganglioside D3, Ganglioside M1, Ganglioside Q1b, Thyroid peroxidase, Thyroglobulin, Glutamate decarboxylase, -cyclic citrullinated peptide, IgG-Fc portion, glycoproteins IIb-IIIa or Ib-IX, ADAMTS13, G1q, Complement Factor H, glutamic acid decarboxylase or a part thereof.

In one aspect the binding region comprises a drug that is used as substitution, or replacement therapy in the treatment of disease.

In one aspect the binding region can bind an antibody produced by plasma cells against a drug, for example a drug administered as replacement or substitution therapy. Such a replacement therapy can be delivery of a body substance (eg in recombinant form) to compensate for the loss of that substance which would normally be produced in a healthy individual, eg where the loss may be as a result of disease or surgery or by way of genetic deficiency, for example. Certain drugs used as replacement therapies can provoke the generation of antibodies which then lead to resistance to the drug, for example as seen in Haemophilia A and Factor VIII resistance. Elimination of such plasma cells to the drug may be beneficial. However, the invention is not limited to such replacement therapies and could in principle apply to elimination of plasma cells generating antibodies to any drug.

In one aspect the binding region comprises a drug used as substitution, or replacement therapy in the treatment of disease such as, but not limited to, Haemophilia A.

In one aspect the binding region is Factor VIII or a part thereof.

The binding region is suitably able to bind to an antibody released from a plasma cell such that the plasma cell is then targeted by the immune system for destruction. This interaction between an antibody from a plasma cell and the binding region may be tested in vitro, in vivo or ex vivo as disclosed in the Examples herein to determine suitable antibodies and doses at which plasma cell killing takes place.

The anchor region of said composition may be associated to the binding region by chemical cross linking. In another aspect the 2 regions may be associated by protein-protein interactions, such as leucine zippers. Alternatively the composition may be a fusion protein comprising an anchor region and a binding region which form a part of the same polypeptide chain. In one aspect the binding region is associated with the anchor region by a covalent bond.

The binding region is associated with the anchor region directly, or indirectly, for example by a linker. A linker may be included where it is desired to introduce a spatial separation between the anchor and binding regions, or introduce some other functionality. The linker may be, for example, a protein linker, a synthetic linker, a polymeric linker or any other suitable linker. The linker may be an amino acid sequence of, for example, 5-500 amino acids.

In another aspect the anchor region and binding region each comprise a part of a linker, for example, the two regions may be linked via a biotin—streptavidin linkage, in which each one of the binding and anchor regions comprise a component of that pair, and the components associate in vivo or in vitro.

In one aspect the association of the binding region with the anchor region is detectable at the surface of the plasma cell in vivo.

Whilst the binding region and the anchor region are suitably delivered together in associated form, for example as a single polypeptide, in one aspect the binding region and anchor region could be separately delivered such that they form an association at the surface of the plasma cell. For example, the anchor could be an antibody, and the binding region itself comprise an antibody portion specific for that first (anchor) antibody.

In a further aspect the composition of the invention may be provided as a nucleic acid such as DNA or RNA which can be delivered and expressed to form a protein composition of the invention. The invention thus also relates to vectors such as expression vectors comprising such nucleic acid sequences and to cells containing said nucleic acids or vectors.

The invention relates to methods using the composition of the invention, for example to target and kill plasma cells expressing antibodies that are associated with diseases.

Thus the invention provides methods and uses as follows:

A method for prevention or treatment of disease caused or exacerbated by an antibody released by a plasma cell, the method comprising delivery to an individual a composition as disclosed herein.

A composition as disclosed herein for use in for prevention or treatment of disease caused or exacerbated by an antibody released by a plasma cell.

Use of a composition as disclosed herein in the preparation of a medicament for the prevention or treatment of disease caused or exacerbated by an antibody released by a plasma cell.

Suitably the composition is delivered to an individual in need thereof in an effective amount to reduce antibody production from the plasma cell to which the composition is bound.

In one aspect the composition disclosed herein is delivered to an individual in need thereof in combination with a medicament capable of preventing the regeneration of plasma cells. Such a medicament may be selected from, for example, an anti CD20 antibody such as rituximab, ocrelizumab, ofatumumab or drugs able to target BLyS and APRIL (for example anti-BLyS such as Belivumab, and TACI-Ig such as Atacicept respectively). Such a combined treatment would serve to kill specific plasma cells producing antibodies associated with disease, as well as prevent the development of new plasma cells generating the same antibody.

The invention thus relates to a composition or polynucleic acid encoding such a composition provided in combination with a medicament capable of preventing the regeneration of plasma cells, optionally wherein the medicament is selected from an anti CD20 antibody such as rituximab, ocrelizumab or ofatumumab or drugs able to target BLyS and APRIL (for example anti-BLyS such as Belivumab, and TACI-Ig such as Atacicept respectively). The 2 components may be for simultaneous, substantially simultaneous or sequential delivery.

In another aspect the methods and uses of the invention comprise treating an individual by plasmapheresis or other methods known to reduce or eliminate serum antibodies prior to delivery of the composition of the invention. Therefore the invention relates to a method or composition as disclosed herein wherein the individual has been previously subjected to a plasmapheresis treatment to reduce or eliminate serum antibodies.

In another aspect the invention provides a method for killing an antibody producing cell in vivo, in vitro or ex vivo comprising contacting, with a composition of the invention, a sample containing a plasma cell, the composition being in an amount effective to result in plasma cell killing. The sample may be a liquid such as blood or plasma, or a solid such as a tissue or part thereof. For example, blood or plasma may be removed from a body and, once removed, treated by the method of the invention.

In one aspect the composition of the invention is provided in an environment capable of effecting complement lysis and/or antibody-dependent cellular cytotoxicity (ADCC).

Therefore the invention also relates to a method for the in vitro-elimination or ex-vivo of an antigen-specific antibody secreting cell, the method comprising contacting a sample comprising an antibody secreting cell with a composition comprising:
an anchor region capable of binding to a plasma cell; and
a binding region associated with the anchor region, wherein the binding region binds a specific plasma antibody.

The invention further relates to the use of compositions of the invention as disclosed herein in the elimination in vivo of specific antibody producing cells, even where such cells and the antibodies they produce are not associated with disease. For example, the compositions may be for use in animal models, for example in situations in which it is desired to remove or reduce plasma cells and the antibodies they produce for reasons unrelated to disease, but which are advantageous for the use of the animal model.

The invention thus relates to a composition comprising:
an anchor region capable of binding to a plasma cell; and
a binding region associated with the anchor region, wherein the binding region is capable of binding a specific plasma cell antibody,
the composition for use in elimination of an antibody released by the plasma cell, wherein the composition is delivered to an individual, such as a human or non-human animal.

The invention thus relates to a method for elimination of an antibody released by a plasma cell, wherein the method comprises delivering to an individual, such as a human or non-human animal, a composition comprising:

an anchor region capable of binding to a plasma cell; and a binding region associated with the anchor region, wherein the binding region binds a specific plasma antibody.

Use of a composition as disclosed herein for the ex vivo or in vitro-elimination of an antigen-specific antibody secreting cell.

Both in vivo, ex vivo and in vitro, the present invention also provides methods in which antibodies, or fragments thereof, may be supplied which are capable of specific interaction with the binding region, rather than (or in addition to) relying upon antibodies release from a plasma cell. For example, when bound to the target plasma cell, the composition of the invention could be contacted with antibodies or fragments thereof which specifically bind to, or are specifically bound by, the binding region. In this way cell killing could be potentially increased.

In vitro, the nature of the interaction between a binding region and antibody can be probed by contacting any plasma cell with composition of the invention and then providing that plasma cell with an antibody directed to the binding region in order to determine the degree of interaction of that antibody with binding region, for example by monitoring the extent of cell killing as a surrogate for the binding efficacy. The efficacy of the antibody—binding region interaction can therefore be probed in vitro, allowing optimisation of the interaction if needed.

Therefore in one further aspect the invention provides a method or use as disclosed herein, the method or use comprising delivering to an individual, or cells, or tissue, a composition of the invention and then further delivering to the individual, cells or tissue respectively, an antibody capable of a specific interaction with the binding region of the composition, optionally followed by measurement of cell killing.

The antibody may be provided in any suitable amount to facilitate cell killing, for example.

The invention the ability to directly identify a plasma cell secreting a specific antibody of interest can be used to select such plasma cells as well as to eliminate these cells.

By way of example, using methods of the invention, cells expressing an antibody of interest will have on the cell surface a composition of the invention bound by such antibodies. Those bound antibodies can be subsequently detected by a probe, such as a labelled probe, such as an anti-Ig antibody labelled with a fluorescent probe, and then identified by suitable techniques, such as FACS analysis for fluorescent labels.

This the invention also provides for a method for identification of a plasma cell of interesting comprising:

1 contacting a sample comprising an antibody secreting plasma cell with a composition, the composition comprising:

- an anchor region capable of binding to a plasma cell; and
- a binding region associated with the anchor region, wherein the binding region is capable of binding a specific plasma cell antibody; and 2 detecting an antibody associated with the composition bound to a plasma cell, for example by use of a labelled detection agent specific for an antibody released from the cell.

This method may be used in combination with any other feature of the present invention.

In another, alternative, aspect a composition may comprise an anchor region which is not limited to binding of plasma cells, but which may be capable of specific binding to another cell type, such as a B cell or T cells. A composition comprising an anchor region capable of specific binding to such a cell may be associated with a binding region, wherein the binding region is capable of binding to a specific antibody. In this way provision of a specific antibody for the binding region can allow the targeting of the cell to which the composition is bound, and facilitate subsequent cell killing, which may occur either in vivo or in vitro. The antibodies may be provided from an exogenous source or may be provided in vivo, for example be an antibody produced by a plasma cell. The cell to be targeted in this aspect may not be a plasma cell which is generating undesirable antibodies, but may be a cell which could be a precursor of that plasma cell, for example, or may be any other cell which is associated with disease, and which it is desired to specifically target using the composition as described as a target for antibody binding and therefore targeted cell killing.

In this alternative aspect there is disclosed:

A composition comprising:

an anchor region capable of specific binding to a cell; and a binding region associated with the anchor region, wherein the binding region is capable of binding a specific antibody.

A method for prevention or treatment of disease the method comprising delivery to an individual a composition comprising:

an anchor region capable of specific binding to a cell; and a binding region associated with the anchor region, wherein the binding region is capable of binding a specific antibody.

A method for the in vitro-elimination of a cell, the method comprising contacting a sample comprising an antibody secreting cell with a composition comprising:

an anchor region capable of specific binding to the cell; and a binding region associated with the anchor region, wherein the binding region is capable of binding a specific antibody.

Use of a composition comprising:

- an anchor region capable of specific binding to a cell; and
- a binding region associated with the anchor region, wherein the binding region is capable of binding to a specific antibody in the preparation of a medicament for prevention or treatment of disease in an individual.

A composition comprising:

an anchor region capable of specific binding to a cell; and a binding region associated with the anchor region, wherein the binding region is capable of binding to a specific antibody, for use in prevention or treatment of disease.

In the alternative aspect described above, anchor regions and binding regions may be associated as described above, and have linkers as described above. The composition may have anchor regions and binding regions broadly as above, noting that the anchor region binding would be to a cell other than a plasma cell, and that binding regions may associate with antibodies that are plasma antibodies (which may be naturally produced or equivalent to naturally produced), or other antibodies, or fragments thereof. Therefore the general disclosure herein in respect of compositions to target plasma cells applies equally to compositions that could be used to target different cell types and any disclosure may be read as a disclosure of a composition for use in the alternative aspect.

The composition of the invention may be delivered by any conventional route of administration, including, but not limited to, intravenous (IV), intramuscular, oral, subcutaneous, intradermal, and parenteral delivery.

In one aspect IV delivery is preferred.

In another aspect the delivery may be targeted to the bone marrow.

The compositions of the present invention may be administered at a daily dosage of from about 0.005 mg to about 100 mg per kg of body weight of the individual, for example given as a single daily dose, or a once weekly dose, or a dose every 2 weeks, three weeks, 1 month, 2 months or 3 months, or more. This dosage regimen may be adjusted to provide the optimal therapeutic response. Suitable individual doses of composition such as polypeptides may include 10-1000 mg, such as 10-100 mg, 100-200 mg, 200-300 mg, 300-400 mg, 400-500 mg, and 500-1000 mg.

It will be understood that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Generally, where the composition is a polypeptide, then the amount of antigen in each dose of composition is selected as an amount which is effective to produce cell killing of cells that are bound by the anchor region without significant, adverse side effects in typical subjects. Such amount may vary depending on which specific polypeptides are employed. An optimal amount for a particular composition can be ascertained by standard studies involving observation of antibody titres and other responses in subjects.

All references or patent applications cited within this patent specification are incorporated by reference herein.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine study, numerous equivalents to the specific procedures described herein. Such equivalents are considered to be within the scope of this invention and are covered by the claims. All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference. The use of the word "a" or an when used in conjunction with the term "comprising" in the claims and/or the specification may mean "one," but it is also consistent with the meaning of "one or more," "at least one," and "one or more than one." The use of the term or in the claims is used to mean "and/or" unless explicitly indicated to refer to alternatives only or the alternatives are mutually exclusive, although the disclosure supports a definition that refers to only alternatives and "and/or." Throughout this application, where relevant, the term "about" is used to indicate that a value includes the inherent variation of error for the device, the method being employed to determine the value, or the variation that exists among the study subjects.

Any feature of the invention is disclosed as a discreet combination with any other feature or features of the invention, unless otherwise apparent from the context.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps The term "or combinations thereof" as used herein refers to all permutations and combinations of the listed items preceding the term. For example, "A, B, C, or combinations thereof is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled person will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

The present examples are not limiting upon the invention.

EXAMPLES

Example 1

Figure 1A:
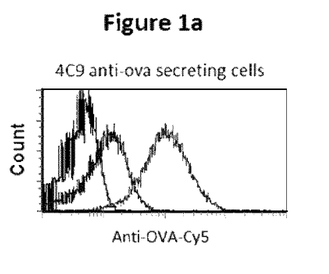
FIG. 1a shows the testing of an anti-CD138-OVA composition (matrix) tested for the binding of the cell surface of the hybridoma.
Figure 1B:
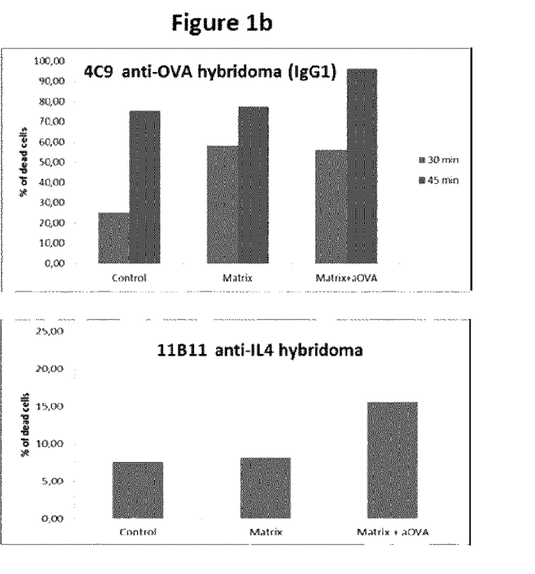
FIG. 1b shows that anti-OVA specific hybridoma cells are lysed in this experimental setting by secreting their own anti-OVA antibody.

As proof of principle we carried out in vitro experiments using OVA-specific hybridoma cell lines. We used four anti-OVA secreting hybridoma clones to demonstrate that the composition can induce selective cell death. We used three clones (1 E10, 2E8, 4G11) producing IgG2b anti-OVA antibodies and one (4C9) producing IgG1 antibodies. We built an anti-CD138-OVA composition (matrix) which was tested for its binding of the cell surface of the hybridoma (FIG. 1a, red line). Then, the self-elimination of ASC was induced in matrix labelled hybridoma cells which were cultivated for 30 (blu-bars) or 45 (red-bars) min at 37° C. to enable antibody secretion and by addition of rabbit complement which binds to the anti-OVA specific antibodies on the matrix-coated ASCs and lyses the cells. The number of dead cells was analyzed by Trypan blue exclusion assay; the stained cells were counted under the microscope and in some experiments the results were confirmed by FACS-analysis. FIG. 1b shows that anti-OVA specific hybridoma cells are lysed in this experimental setting by secreting their own anti-OVA antibodies. Instead, a hybridoma of another specificity (anti IL-4, clone 11B11) can be indeed lysed but only by external addition of anti-OVA antibodies.

Figure 2:
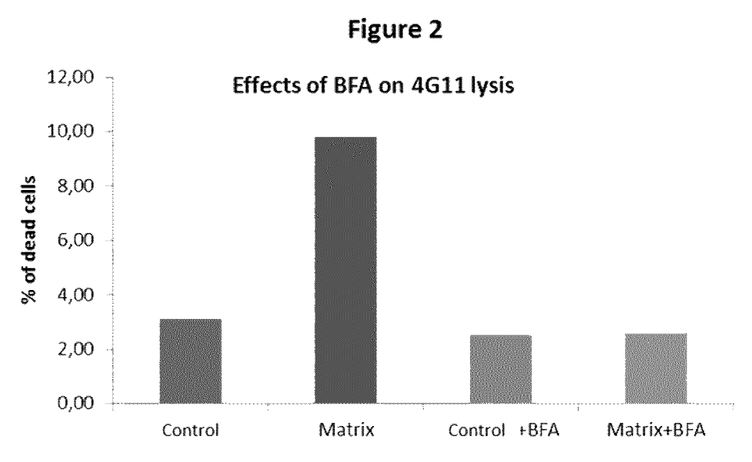
FIG. 2 shows the addition of Brefeldin A to the cell culture inhibits vesicle transport and thus the transport of intracellular antibody out of the cell.

A further proof that the cell lysis is dependent on antibody secretion is shown by addition of Brefeldin A to the cell culture which inhibits the vesicle transport and thus the transport of intracellular antibody out of the cell (FIG. 2).

Figure 3:
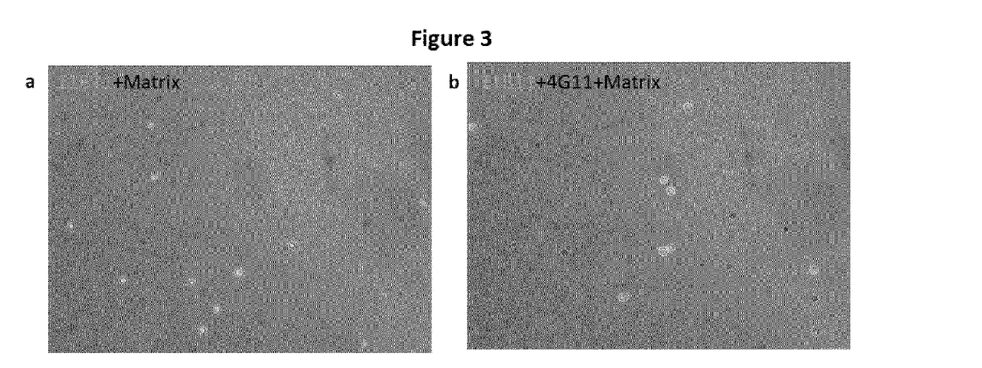
FIG. 3 shows a micrograph of co-cultures of OVA-specific hybridoma cells and a cell line of another specificity, which was labelled prior with a CFSE fluorescent marker. Both hybridoma lines were labelled with the anti-CD138/OVA MATRIX. The micrograph identifies the specific killing of only the OVA-specific cell line. Panel "a" features a micrograph where the anti-CD138/OVA (MATRIX) was present. Panel "b" features a micrograph where both anti-OVA (4G11) and anti-CD138/OVA (MATRIX) was present.

One problem of the system, especially when carried out in in vivo models, could be the binding of the matrix to ASC of foreign specificity and a subsequent lysis of these unspecific ASC by specific neighbouring ASC. The high specificity of the antigen-driven self-elimination of the anti-OVA secreting cells was proved in a mixed culture system. OVA-specific hybridoma cells were cultured together with a cell line of another specificity which was labelled before with the fluorescent marker CFSE. Both hybridomas were labelled with the anti-CD138/OVA matrix. In this system, the specific killing of only the OVA-specific cell line could be shown using the combined fluorescence/light microscopy (FIG. 3). This is the sine qua non for the applicability of this system in vivo.

Moreover, to verify that the effect of depletion is maintained also using another antibody rather anti-CD138, we generated a new matrix using the Fab fragment anti-CD44. As shown in FIG. 4, the cellular-affinity matrix built with an anti-CD44 fab-fragment is able to induce a specific lysis in anti-ova secreting hybridoma (4G11) and not in an unspecific hybridoma (11B11).

Example 2

One of the most time and labor intensive procedure in the production of monoclonal antibodies (mAbs) by hybridoma cell lines is the identification of antigen-specific antibody-producing clones within a heterogeneous cell population. Moreover, some hybridomas can lose the ability to produce mAbs by continuous culture and recloning is therefore recommended if hybridomas have been in culture for a long period of time and monoclonality or stability of the hybridoma needs to be confirmed. Indeed, despite their biological and practical significance, only a few methods are presently available for the analysis of secreted antibody on the single cell level by antibody secreting cells (ASCs). These methods may offer a valid alternative for selecting the antigen-specific cells allowing a faster and more accurate selection of the clones of interest. Here we describe a new concept for cytometry and sorting of live ASCs based on the specificity of the produced antibody. Basically, the secreted antibody is retained on the cell surface of the secreting cell, making it accessible to the powerful technologies for detection of surface markers. ASCs were incubated with an affinity matrix composed of 1) an antibody binding. For this proof-of concept experiment an anti-CD138-OVA-construct (affinity matrix) was generated and anti-OVA secreting hybridoma clones were used as model of ASCs. Anti-OVA IgG1 secreting hybridoma cells were mixed at different ratio (from 2:1 to 1:10000) with aspecific cells (X63-Ag6.653 myeloma cells or anti-OVA IgG2a secreting cells). After a short incubation for allowing the antibody secretion, the anti-OVA antibodies secreted by ASC binds to the antigen brought to the surface of the ASC by our matrix. The OVA-specific ASCs were then stained with a fluorochrome labeled anti-IgG1 antibody and visualized by FACS. The affinity matrix technology allowed us to clearly show a specific labeling of cells producing antibodies with the desired specificity and the desired IgG subclass independently of the ratio of specific/aspecific cells. These results show that using the affinity matrix technology it is possible to select ASCs in an antigen-specific way. Therefore, this technology represents a useful tool for reducing the time and manipulations necessary for hybridoma selection and cloning and provides an innovative method for the analysis of secreted antibody on the single cell level by antibody secreting cells (i.e. hybridoma cells and plasma cells).

REFERENCES

1. Hiepe, F., T. Dorner, A. E. Hauser, B. F. Hoyer, H. Mei, and A. Radbruch. 2011. Long-lived autoreactive plasma cells drive persistent autoimmune inflammation. Nat Rev Rheumatol 7: 170-178.
2. Radbruch, A., G. Muehlinghaus, E. O. Luger, A. Inamine, K. G. Smith, T. Dorner, and F. Hiepe. 2006. Competence and competition: the challenge of becoming a long-lived plasma cell. Nat Rev Immunol 6: 741-750.
3. Alexander, T., A. Thiel, O. Rosen, G. Massenkeil, A. Sattler, S. Kohler, H. Mei, H. Radtke, E. Gromnica-Ihle, G. R. Burmester, R. Arnold, A. Radbruch, and F. Hiepe. 2009. Depletion of autoreactive immunologic memory followed by autologous hematopoietic stem cell transplantation in patients with refractory SLE induces long-term remission through de novo generation of a juvenile and tolerant immune system. Blood 113: 214-223.
4. Neubert, K., S. Meister, K. Moser, F. Weisel, D. Maseda, K. Amann, C. Wiethe, T. H. Winkler, J. R. Kalden, R. A. Manz, and R. E. Voll. 2008. The proteasome inhibitor bortezomib depletes plasma cells and protects mice with lupus-like disease from nephritis. Nat Med 14: 748-755.
5. DiLillo, D. J., Y. Hamaguchi, Y. Ueda, K. Yang, J. Uchida, K. M. Haas, G. Kelsoe, and T. F. Tedder. 2008. Maintenance of long-lived plasma cells and serological memory despite mature and memory B cell depletion during CD20 immunotherapy in mice. J Immunol 180: 361-371.

The invention claimed is:

1. A method for the treatment or prevention of a disease caused or exacerbated by an antibody released by a plasma cell comprising delivering to an individual a composition comprising:
   an anchor region, wherein the anchor region is an antibody, a (Fab')$_2$, monovalent Fab, single chain antibody, single chain Fv (scFv), or single domain antibody, which specifically binds CD138; and
   a binding region associated with the anchor region, wherein the binding region is capable of binding a specific plasma cell antibody such that the plasma cell is targeted by the individual's immune system for destruction and wherein the binding region comprises an autoantigen selected from the group consisting of nicotinic acetylcholine receptor, muscarinic acetylcholine receptor M1, MuSK protein, myelina associated glycoprotein, 17 hydroxylase, 21 hydroxylase, cardiolipin, β2 glycoprotein I, phosphatidyl-serine, apoH, annexin A5, voltage-dependent calcium channel, ganglioside D3, ganglioside M1, ganglioside Q1b, thyroid peroxidase, thyroglobulin, glutamate decarboxylase, cyclic citrullinated peptide, IgG-Fc, glycoproteins IIb-IIIa or Ib-IX, ADAMTS13, C1q, complement factor H, and glutamic acid decarboxylase.

2. The method of claim 1 wherein the binding region is capable of binding to a variable region of the specific plasma cell antibody.

3. The method of claim 1 wherein the autoantigen is nicotinic acetylcholine receptor or muscarinic acetylcholine receptor M1.

4. The method of claim 1 wherein the anchor region and the binding region are associated via a linker.

5. The method of claim 1 wherein the anchor region and binding region form part of the same polypeptide.

6. A method for the treatment or prevention of a disease caused or exacerbated by an antibody released by a plasma cell comprising delivering to an individual a nucleic acid encoding a composition comprising:

an anchor region, wherein the anchor region is an antibody, a $(Fab')_2$, monovalent Fab, single chain antibody, single chain Fv (scFv), or single domain antibody, which specifically binds CD138 on a plasma cell; and a binding region associated with the anchor region, wherein the binding region is capable of binding a specific plasma cell antibody such that the plasma cell is targeted by the individual's immune system for destruction and wherein the binding region comprises an autoantigen selected from the group consisting of nicotinic acetylcholine receptor, muscarinic acetylcholine receptor M1, MuSK protein, myelina associated glycoprotein, 17 hydroxylase, 21 hydroxylase, cardiolipin, β2 glycoprotein I, phosphatidylserine, apoH, annexin A5, voltage-dependent calcium channel, ganglioside D3, ganglioside M1, ganglioside Q1b, thyroid peroxidase, thyroglobulin, glutamate decarboxylase, cyclic citrullinated peptide, IgG-Fc, glycoproteins IIb-IIIa or Ib-IX, ADAMTS13, C1q, complement factor H, and glutamic acid decarboxylase.

7. The method of claim 6 wherein the nucleic acid is provided in combination with an additional pharmaceutically active agent capable of preventing the regeneration of plasma cells.

8. The method of claim 7, wherein the additional pharmaceutically active agent is an anti-CD20 antibody.

9. The method of claim 8 wherein the anti-CD20 antibody is rituximab, ocrelizumab or ofatumumab.

10. The method of claim 7 wherein the additional pharmaceutically active agent capable of targeting BLyS or APRIL.

11. The method of claim 10 wherein the additional pharmaceutically active agent capable of targeting BLyS is Belivumab.

12. The method of claim 11 wherein the additional pharmaceutically active agent capable of targeting APRIL is Atacicept.

13. The method of claim 6 wherein the individual has been previously subjected to a plasmapheresis treatment to reduce or eliminate serum antibodies.

14. The method of claim 6 wherein the individual is treated with an additional pharmaceutically active agent capable of preventing the regeneration of plasma cells.

15. A method for elimination of an antibody released by a plasma cell comprising delivering to an individual a composition comprising:

an anchor region, comprising an antibody, a $(Fab')_2$, monovalent Fab, single chain antibody, single chain Fv (scFv), or single domain antibody, which specifically binds CD138 expressed on a plasma cell; and a binding region associated with the anchor region, wherein the binding region is capable of binding a specific plasma cell antibody such that the plasma cell is targeted by the individual's immune system for destruction and wherein the binding region comprises an autoantigen selected from the group consisting of nicotinic acetylcholine receptor, muscarinic acetylcholine receptor M1, MuSK protein, myelina associated glycoprotein, 17 hydroxylase, 21 hydroxylase, cardiolipin, β2 glycoprotein I, phosphatidylserine, apoH, annexin A5, voltage-dependent calcium channel, ganglioside D3, ganglioside M1, ganglioside Q1b, thyroid peroxidase, thyroglobulin, glutamate decarboxylase, cyclic citrullinated peptide, IgG-Fc, glycoproteins IIb-IIIa or Ib-IX, ADAMTS13, C1q, complement factor H, and glutamic acid decarboxylase.

16. The method of claim 15 wherein said method is carried out in vivo.

17. The method of claim 15 wherein the autoantigen is nicotinic acetylcholine receptor or muscarinic acetylcholine receptor M1.

18. The method of claim 15 wherein the anchor region and the binding region are associated via a linker.

19. The method of claim 15 wherein the anchor region and binding region comprise the same polypeptide.

* * * * *

UNITED STATES PATENT AND TRADEMARK OFFICE
CERTIFICATE OF CORRECTION

PATENT NO. : 9,862,772 B2  Page 1 of 1
APPLICATION NO. : 14/426650
DATED : January 9, 2018
INVENTOR(S) : Andreas Radbruch et al.

It is certified that error appears in the above-identified patent and that said Letters Patent is hereby corrected as shown below:

On the Title Page

At (73) Assignee Line 1: replace "BEUTSCHES" with --DEUTSCHES--.

Signed and Sealed this
Twenty-ninth Day of May, 2018

Andrei Iancu
*Director of the United States Patent and Trademark Office*